(12) United States Patent
Takada

(10) Patent No.: US 9,968,914 B2
(45) Date of Patent: May 15, 2018

(54) METHOD FOR PRODUCING OLEFIN

(71) Applicant: KAO CORPORATION, Tokyo (JP)

(72) Inventor: Shingo Takada, Wakayama (JP)

(73) Assignee: KAO CORPORATION, Tokyo (JP)

( * ) Notice: Subject to any disclaimer, the term of this patent is extended or adjusted under 35 U.S.C. 154(b) by 0 days. days.

(21) Appl. No.: 14/655,534

(22) PCT Filed: Dec. 19, 2013

(86) PCT No.: PCT/JP2013/084164
§ 371 (c)(1),
(2) Date: Jun. 25, 2015

(87) PCT Pub. No.: WO2014/103898
PCT Pub. Date: Jul. 3, 2014

(65) Prior Publication Data
US 2015/0353442 A1    Dec. 10, 2015

(30) Foreign Application Priority Data

Dec. 26, 2012  (JP) ................................ 2012-282969

(51) Int. Cl.
| | | |
|---|---|---|
| C07C 1/24 | (2006.01) | |
| C07C 303/20 | (2006.01) | |
| B01J 27/053 | (2006.01) | |
| C07F 9/6568 | (2006.01) | |
| B01J 23/30 | (2006.01) | |
| B01J 27/16 | (2006.01) | |
| C07C 303/32 | (2006.01) | |
| B01J 21/12 | (2006.01) | |
| B01J 35/10 | (2006.01) | |
| B01J 37/02 | (2006.01) | |
| B01J 23/00 | (2006.01) | |
| B01J 35/00 | (2006.01) | |
| B01J 21/04 | (2006.01) | |
| B01J 23/10 | (2006.01) | |

(52) U.S. Cl.
CPC .......... *B01J 27/053* (2013.01); *B01J 21/12* (2013.01); *B01J 23/002* (2013.01); *B01J 23/30* (2013.01); *B01J 27/16* (2013.01); *B01J 35/002* (2013.01); *B01J 35/1019* (2013.01); *B01J 35/1038* (2013.01); *B01J 35/1042* (2013.01); *B01J 35/1047* (2013.01); *B01J 35/1061* (2013.01); *B01J 37/0236* (2013.01); *C07C 1/24* (2013.01); *C07C 303/20* (2013.01); *C07C 303/32* (2013.01); *C07F 9/65685* (2013.01); *B01J 21/04* (2013.01); *B01J 23/10* (2013.01); *C07C 2521/04* (2013.01); *C07C 2521/06* (2013.01); *C07C 2521/12* (2013.01); *C07C 2523/30* (2013.01); *C07C 2527/02* (2013.01); *C07C 2527/053* (2013.01); *C07C 2527/14* (2013.01); *C07C 2527/167* (2013.01)

(58) Field of Classification Search
None
See application file for complete search history.

(56) References Cited

U.S. PATENT DOCUMENTS

| | | | |
|---|---|---|---|
| 3,246,045 A | 4/1966 | Hoffman et al. | |
| 3,376,336 A | 4/1968 | Stein et al. | |
| 3,423,453 A | 1/1969 | Baumann et al. | |
| 3,888,918 A | 6/1975 | Kuehnhanss | |
| 4,207,424 A * | 6/1980 | Winnick ................... | B01J 21/12 585/357 |
| 4,234,752 A | 11/1980 | Wu et al. | |
| 4,302,357 A | 11/1981 | Kojima et al. | |
| 4,677,095 A * | 6/1987 | Wan ..................... | B01D 53/945 502/262 |
| 5,650,544 A | 7/1997 | Ariyoshi et al. | |
| 5,907,066 A * | 5/1999 | Wachs ............... | B01D 53/8668 162/16 |
| 2004/0121902 A1* | 6/2004 | Chang ..................... | B01J 29/83 502/208 |
| 2004/0267073 A1 | 12/2004 | Zander et al. | |
| 2007/0299291 A1 | 12/2007 | Koivusalmi | |
| 2008/0027262 A1 | 1/2008 | Meudt et al. | |
| 2008/0058572 A1 | 3/2008 | Fernandez et al. | |
| 2008/0287722 A1 | 11/2008 | Dierker | |
| 2011/0056656 A1 | 3/2011 | Ziehe et al. | |
| 2011/0098519 A1* | 4/2011 | Ramesh ................ | B01J 27/182 585/640 |

(Continued)

FOREIGN PATENT DOCUMENTS

| | | |
|---|---|---|
| CN | 101940938 A | 1/2011 |
| DE | 583 564 C | 9/1933 |

(Continued)

OTHER PUBLICATIONS

Maciver et al., "Catalytic Aluminas I. Surface Chemistry of Eta and Gamma Alumina", Journal of Catalysis, 2, 1963, pp. 485-497.*
Sinkler et al. ("3D-TEM study of gamma alumina catalyst supports", Micros. Microanal, 12 (Supp 2), 2006, pp. 52-53).*
Bolder et al., "Dehydration of Alcohols in the Presence of Carbonyl Compounds and Carboxylic Acids in a Fischer-Tropsch Hydrocarbons Matrix," Applied Catalysis A: General, (2006), Available Online Dec. 6, 2005, vol. 300, pp. 36-40.
Chinese Office Action and Search Report, issued Nov. 6, 2013, for Chinese Application No. 201080048811.9.
Extended European Search Report, dated Jun. 2, 2014, for European Application No. 10826862.4.
International Search Report, dated Nov. 30, 2010 for International Application No. PCT/JP2010/069314.
Japanese Office Action, dated Sep. 4, 2012, for Japanese Application No. 2011-538501, along with an English translation.

(Continued)

Primary Examiner — Rosalynd A Keys
(74) Attorney, Agent, or Firm — Birch, Stewart, Kolasch & Birch, LLP

(57) ABSTRACT

The present invention relates to a process for producing olefins, including the step of subjecting an alcohol having not less than 8 and not more than 22 carbon atoms to dehydration reaction in the presence of a solid acid catalyst, in which the solid acid catalyst includes aluminum oxide and an oxide of an element having an electronegativity higher than that of aluminum which is supported on the aluminum oxide.

15 Claims, No Drawings

(56) References Cited

U.S. PATENT DOCUMENTS

2012/0220808 A1  8/2012  Takada

FOREIGN PATENT DOCUMENTS

| | | |
|---|---|---|
| DE | 705 179 C | 4/1941 |
| DE | 247 895 A1 | 7/1987 |
| EP | 0 150 832 A2 | 8/1985 |
| JP | 53-33602 B1 | 9/1978 |
| JP | 59-040057 B2 | 9/1984 |
| JP | 61-53230 A | 3/1986 |
| JP | 2-306956 A | 12/1990 |
| JP | 8-143497 A | 6/1996 |
| JP | 9-157200 A | 6/1997 |
| JP | 10-167993 A | 6/1998 |
| JP | 11-514337 A | 12/1999 |
| JP | 2001-114749 A | 4/2001 |
| JP | 2008-503453 A | 2/2008 |
| JP | 2008-056671 A | 3/2008 |
| JP | 2012-232944 A | 11/2012 |
| JP | 2013-203704 A | 10/2013 |
| JP | 2013-234139 A | 11/2013 |
| SK | 2346-92 A3 | 2/1995 |
| SK | 280789 B6 | 7/2000 |
| WO | WO 97/03932 A1 | 2/1997 |
| WO | WO 01/44145 A1 | 6/2001 |
| WO | WO 2007/144473 A1 | 12/2007 |
| WO | WO 2009/092349 A2 | 7/2009 |
| WO | WO 2011/052732 A1 | 5/2011 |
| WO | WO 2011/161045 A1 | 12/2011 |

OTHER PUBLICATIONS

Komarewsky, et al,, "Catalytic Dehydration of 1-Hexanol and 1-Octanol," Journal of the American Chemical Society, vol. 67, Apr. 1, 1945, pp. 557-558, XP-055119289.

Solomon, et al., "Catalysis of Alcohol and Ether Dehydration on Gamma-Alumina," I&EC Fundamentals, vol. 6, No. 3, Aug. 1967 pp. 325-333.

Walker, "Vapor-Phase Dehydration of Dodecanol over Alumina," Industrial and Engineering Chemistry, vol. 41, No. 11, Nov. 1949, pp. 2640-2644, XP-055119292.

Chokkaram et al., "Conversion of 2-octanol over nickel-alumina, cobalt-alumina, and alumina catalysts", Journal of Molecular Catalysis A: Chemical, vol. 121, Issues 2-3, 1997, pp. 157-169.

Davis, Burtron H., "The Olefin Selectivity for the Dehydration of 2-Octanol by Alumina and Thoria", The Journal of Organic Chemistry, vol. 37, No. 8, 1972, pp. 1240-1244.

International Search Report issued in PCT/JP2013/084164, dated Mar. 25, 2014.

Mastagli, Pierre, "Action déshydratante de l'acide tungstique en phase liquide sur les alcools primaires, secondaires et tertiaires", Comptes Rendus de l'Academie des sciences, vol. 248, No. 9, 1959, pp. 1352-1354.

Weil et al., "Sulfonation of Hexadecene-1 and Octadecene-1", The Journal of the American Oil Chemists' Society, vol. 42, No. 10, Oct. 1965, pp. 873-875.

Author Unknown, "Periodic Table of Elements," Electronegativity, Chemicals Manual Basic Volume, 5th Edition, 2001, 1 page.

* cited by examiner

METHOD FOR PRODUCING OLEFIN

FIELD OF THE INVENTION

The present invention relates to a process for producing long-chain olefins.

BACKGROUND OF THE INVENTION

There are known various processes for producing olefin compounds by dehydration reaction of alcohols. For example, Patent Literature 1 discloses a process for producing an olefin compound by subjecting a tertiary alcohol to dehydration reaction in a gas phase at a temperature of from 200 to 400° C. in the presence of an aluminosilicate as a solid catalyst.

In addition, Patent Literature 2 discloses a process for producing ethylene by subjecting ethanol to dehydration reaction in a gas phase in the presence of a catalyst prepared by adding a phosphate to an active alumina.

On the other hand, the present inventors have found that olefins can be produced for a short period of time with a high yield by subjecting a long-chain alcohol to liquid-phase dehydration reaction using a catalyst having specific weak acid sites, such as γ-alumina, and previously filed a patent application relating thereto (refer to Patent Literature 3).

CITATION LIST

Patent Literature

Patent Literature 1: JP 2008-56671A
Patent Literature 2: JP 59-40057B
Patent Literature 3: WO 2011/052732A

SUMMARY OF THE INVENTION

The present invention relates to a process for producing olefins, including the step of subjecting an alcohol having not less than 8 and not more than 22 carbon atoms to dehydration reaction in the presence of a solid acid catalyst, in which the solid acid catalyst includes aluminum oxide and an oxide of an element having an electronegativity higher than that of aluminum which is supported on the aluminum oxide.

DETAILED DESCRIPTION OF THE INVENTION

However, in the gas phase reaction such as typically the processes described in Patent Literatures 1 and 2, it is required to vaporize a whole amount of the raw material used therein, so that, in particular, when vaporizing the long-chain aliphatic alcohol having a high boiling point, a large energy consumption is needed, which is disadvantageous in view of costs. Further, the silica-alumina catalyst used in Patent Literature 1 tends to cause branching of the olefins owing to alkyl rearrangement along with production of multimers of the olefins, so that there tends to arise such a problem that a yield of the aimed reaction product is lowered. In addition, in Patent Literature 2, it is merely described to suppress deposition of carbonaceous substances, but there is no description concerning suppression of branching of the olefins owing to alkyl rearrangement and production of multimers of the olefins.

The olefins produced by the process described in Patent Literature 3 contain merely a small amount of by-products produced owing to production of multimers or branching. However, it has been further demanded to develop a process for producing olefins with a still higher efficiency.

The present invention relates to a process for producing long-chain olefins for a short period of time with a high efficiency by subjecting a long-chain aliphatic alcohol to dehydration reaction.

The present inventors have found that when subjecting a long-chain aliphatic alcohol to dehydration reaction in the presence of a specific catalyst, it is possible to produce long-chain olefins for a short period of time with a high yield.

More specifically, the process for producing olefins according to the present invention is such a process in which an alcohol is subjected to dehydration reaction in the presence of a solid acid catalyst to produce olefins. The solid acid catalyst is constructed of aluminum oxide and an oxide of an element having an electronegativity higher than that of aluminum which is supported on the aluminum oxide.

The production process of the present invention can provide a process for producing long-chain olefins for a short period of time with a high yield and a high selectivity by subjecting a long-chain aliphatic alcohol to dehydration reaction.

The process for producing olefins according to the present invention is a process for producing olefins by subjecting an alcohol to dehydration reaction using a solid acid catalyst prepared by supporting an oxide of an element having an electronegativity higher than that of aluminum on aluminum oxide.

[Catalyst]

In the present invention, there is used the solid acid catalyst prepared by supporting an oxide of an element having an electronegativity higher than that of aluminum on aluminum oxide. Meanwhile, the value of the electronegativity as used in the present invention means the value of a Pauling electronegativity.

The electronegativity of the solid acid catalyst is preferably not less than 1.6, more preferably not less than 1.7, and still more preferably not less than 1.8, and is also preferably not more than 2.6, and more preferably not more than 2.0, from the viewpoint of suppressing occurrence of side reactions.

Examples of the element having an electronegativity higher than that of aluminum (Al: 1.5) include sulfur (S: 2.5), tungsten (W: 1.7), phosphorus (P: 2.1), silicon (Si: 1.8), molybdenum (Mo: 1.8), iron (Fe: 1.8), cobalt (Co: 1.8), nickel (Ni: 1.8), copper (Cu: 1.9), zinc (Zn: 1.6), boron (B: 2.0), gallium (Ga: 1.6), indium (In: 1.7), germanium (Ge: 1.8), tin (Sn: 1.8), antimony (Sb: 1.9), bismuth (Bi: 1.9) and selenium (Se: 2.4). Of these elements, from the viewpoint of suppressing occurrence of side reactions, preferred are sulfur (S), tungsten (W), phosphorus (P) and silicon (Si). Meanwhile, the numeral value in the above respective parentheses denotes the value of a Pauling electronegativity of the element.

As the compound as an oxide source of the element, from the viewpoint of a good catalytic activity, preferred is at least one compound selected from the group consisting of a water-soluble ammonium salt, a metal alkoxide, and an oxo acid and a salt thereof. Specific examples of the compound as an oxide source of the element include water-soluble ammonium salts such as ammonium sulfate and ammonium tungstate, metal alkoxides that are rendered water-soluble when hydrolyzed, such as tetramethyl orthosilicate and tetraethyl orthosilicate, and oxo acids such as silicotungstic acid and phosphotungstic acid and salts thereof. Meanwhile, the catalytic activity as used herein means a reaction rate of the above dehydration reaction according to the present invention when using the above catalyst therein.

Further specific examples of the compound as an oxide source of the element include at least one compound selected from the group consisting of sulfuric acid, ammonium sulfate, sodium sulfate, potassium sulfate, magnesium sulfate, calcium sulfate, sodium thiosulfate, ammonium thiosulfate, tungstic acid, ammonium tungstate, sodium tungstate, potassium tungstate, calcium tungstate, ammonium paratungstate, ammonium metatungstate, silicotungstic acid, phosphotungstic acid, ammonium phosphotungstate, sodium phosphotungstate, potassium phosphotungstate, colloidal silica, silica gel, water glass, tetramethyl ammonium silicate, tetramethyl orthosilicate, tetraethyl orthosilicate, phosphoric acid, ammonium phosphate, diammonium hydrogen phosphate, sodium phosphate, potassium phosphate, magnesium phosphate and calcium phosphate.

Of these compounds, from the viewpoint of a good catalytic activity, ammonium sulfate, ammonium tungstate, diammonium hydrogen phosphate and tetraethyl orthosilicate are preferably used as an oxide source of the element. When using such a catalyst, the dehydration reaction of the long-chain alcohol proceeds rapidly, so that the long-chain olefins as the aimed product can be produced with a high yield.

The amount of the oxide of the element supported on aluminum oxide is preferably not less than 0.01% by mass, more preferably not less than 0.1% by mass, still more preferably not less than 0.5% by mass, and even still more preferably not less than 0.8% by mass, on the basis of the amount of the aluminum oxide, from the viewpoint of a good catalytic activity. Also, from the same viewpoint, the amount of the oxide of the element supported on aluminum oxide is preferably not more than 10% by mass, more preferably not more than 9% by mass, still more preferably not more than 8% by mass, even still more preferably not more than 7% by mass, and further even still more preferably not more than 2% by mass, on the basis of the amount of the aluminum oxide.

When the amount of the oxide of the element supported on aluminum oxide lies within the above-specified range, it is possible to complete the reaction for a short period of time.

The catalyst used in the present invention may be prepared by an evaporation-to-dryness method, an adsorption method, an equilibrium adsorption method, a pore filling method, a spraying method, a precipitation method or the like.

As the specific method for preparing the catalyst, from the viewpoint of a good catalytic activity thereof, there may be mentioned the method including the steps of mixing an aqueous suspension or a hydrous solid of the aluminum oxide, a compound as an oxide source of the element or the oxide of the element, and ion-exchanged water to prepare an impregnated product, and drying and calcining the resulting impregnated product. Meanwhile, the aluminum oxide acting as a carrier may be produced, for example, by a precipitation method, a sol-gel method or an alkoxide method. From the viewpoint of a good catalytic activity of the resulting catalyst, the aluminum oxide used above is preferably in the form of a calcined product obtained by calcining it at a temperature of not lower than 400° C., more preferably not lower than 450° C., and still more preferably not lower than 500° C. From the same viewpoint, the temperature of the calcination is also preferably not higher than 900° C., more preferably not higher than 850° C., and still more preferably not higher than 800° C. In the present invention, from the viewpoint of a good catalytic activity of the resulting catalyst, the aluminum oxide is preferably γ-alumina.

The temperature at which the aluminum oxide is impregnated with the compound as an oxide source of the element or the oxide of the element is preferably not lower than 0° C., more preferably not lower than 20° C., still more preferably not lower than 50° C., and even still more preferably not lower than 60° C., and is also preferably not higher than 100° C., more preferably not higher than 95° C., still more preferably not higher than 90° C., and even still more preferably not higher than 80° C., from the viewpoints of a high supporting velocity and a uniformity of the resulting catalyst.

The time of the impregnation is preferably not less than 0.1 h, more preferably not less than 0.2 h, and still more preferably not less than 0.5 h, and is also preferably not more than 10 h, more preferably not more than 5 h, and still more preferably not more than 2 h, from the viewpoints of a high supporting velocity and a uniformity of the resulting catalyst.

The temperature of calcination of the impregnated product is preferably not lower than 300° C., more preferably not lower than 400° C., still more preferably not lower than 450° C., from the viewpoint of a good catalytic activity of the resulting catalyst, and is also preferably not higher than 900° C., more preferably not higher than 850° C., still more preferably not higher than 800° C., even still more preferably not higher than 700° C., and further even still more preferably not higher than 600° C., from the viewpoints of preventing reduction in surface area of the resulting catalyst and attaining a high degree of dispersion of the element to be supported.

The time of calcination of the impregnated product is preferably not less than 1 h, and more preferably not less than 2 h, from the viewpoint of a good catalytic activity of the resulting catalyst, and is also preferably not more than 10 h, and more preferably not more than 5 h, from the viewpoints of preventing reduction in surface area of the resulting catalyst and attaining a high degree of dispersion of the element to be supported.

The atmosphere used upon the calcination is not particularly limited, and the calcination may be carried out in an inert gas atmosphere, an oxidizing atmosphere or a reducing atmosphere. Further, the calcination may be carried out in a closed condition or in a gas-flowing condition. In the present invention, from the viewpoint of a good catalytic activity of the resulting catalyst, the calcination is preferably carried out in a gas flow of air or oxygen.

The thus obtained catalyst is held in an aggregated state and therefore may be appropriately pulverized into a powder or granules or molded into noodles, pellets, etc., upon use.

When the catalyst is used in the form of a powder, the average particle size of the powder is preferably not less than 1 μm, more preferably not less than 5 μm, still more preferably not less than 10 μm, even still more preferably not less than 20 μm, and further even still more preferably not less than 30 μm, from the viewpoint of facilitated recovery of the catalyst after completion of the reaction, and is also preferably not more than 300 μm, more preferably not more than 250 μm, still more preferably not more than 200 μm, even still more preferably not more than 150 μm, further even still more preferably not more than 100 μm, and further even still more preferably not more than 50 μm, from the viewpoint of a good catalytic activity of the resulting catalyst.

The BET specific surface area of the catalyst is preferably not less than 100 m²/g, more preferably not less than 120 m²/g, and still more preferably not less than 140 m²/g, from the viewpoint of a good catalytic activity of the resulting catalyst, and is also preferably not more than 500 m²/g, more preferably not more than 400 m²/g, still more preferably not more than 300 m²/g, and even still more preferably not more than 200 m²/g, from the viewpoints of a good durability and a high strength of the resulting catalyst.

The average pore size of the catalyst is preferably not less than 5 nm, more preferably not less than 7 nm, and still more preferably not less than 9 nm, from the viewpoint of a good catalytic activity of the resulting catalyst, and is also preferably not more than 50 nm, more preferably not more than 40 nm, still more preferably not more than 25 nm, even still more preferably not more than 20 nm, and further even still more preferably not more than 15 nm, from the same viewpoint.

The pore volume of the catalyst is preferably not less than 0.20 cm³/g, more preferably not less than 0.25 cm³/g, and still more preferably not less than 0.30 cm³/g, from the viewpoint of a good catalytic activity of the resulting catalyst, and is also preferably not more than 2.0 cm³/g, more preferably not more than 1.5 cm³/g, still more preferably not more than 1.2 cm³/g, even still more preferably not more than 1.0 cm³/g, and further even still more preferably not more than 0.7 cm³/g, from the same viewpoint.

The average particle size is a median particle size of the catalyst as determined as follows. That is, 0.05 g of the catalyst is dispersed while stirring in ethanol (available from Kanto Chemical Co., Inc.; Cica-First Grade Reagent) as a measuring solvent to measure particle sizes thereof (stirring rate: level 4) using a laser diffraction scattering particle size distribution analyzer "LA-920" (available from HORIBA Ltd.), and a median particle size of the catalyst is calculated from the thus measured particle sizes assuming that the refractive index of the catalyst is 1.10.

Meanwhile, the BET specific surface area, average pore size and pore volume of the catalyst may be measured by the following methods. That is, using an accelerated surface area porosimetry analyzer "ASAP2020" available from Micromeritics Instrument Corp., a sample is heat-treated at 250° C. for 5 h and then a BET specific surface area of the sample is measured by a multi-point method using a liquid nitrogen to obtain its value in such a range that a parameter C is positive.

The pore volume of the catalyst may be calculated by a BJH method (Barrett-Joyner-Halenda method), and further a peak top of a pore distribution curve for the catalyst is defined as an average pore size thereof. The BJH method as used herein is such a method in which the pore volume is calculated from that of a cylindrical pore as a model pore which is not linked with any other pore to determine a pore distribution by capillary condensation and multilayer adsorption of a nitrogen gas. The details of the BJH method are described in "SHIMADZU Review", Vol. 48, No. 1, pp. 35 to 44, 1991.

The amount of the catalyst used in a suspended bed reaction is preferably not less than 0.1% by mass, more preferably not less than 0.3% by mass, still more preferably not less than 0.5% by mass, and even still more preferably not less than 2% by mass, and is also preferably not more than 30% by mass, more preferably not more than 20% by mass, still more preferably not more than 15% by mass, and even still more preferably not more than 12% by mass, on the basis of the alcohol as the raw material. When the amount of the catalyst used lies within the above-specified range, it is possible to reduce the reaction temperature and therefore provide an economically advantageous process.

The details of the mechanism of the reaction using the aforementioned catalyst are still unclear, but it is considered that the reaction proceeds as follows. That is, it is considered that the aluminum oxide is appropriately increased in acid strength by the action of the element supported thereon which has a higher electronegativity, so that the reaction activity is enhanced.

[Alcohol as Raw Material]

The number of carbon atoms contained in the alcohol used as a raw material in the present invention is preferably not less than 8, more preferably not less than 12, and still more preferably not less than 14, and is also preferably not more than 22, more preferably not more than 20, and still more preferably not more than 18, from the viewpoint of usefulness of the resulting olefins. In addition, from the same viewpoint, the number of carbon atoms contained in the alcohol is not less than 8 and not more than 22, preferably not less than 12 and not more than 20, and more preferably not less than 14 and not more than 18. The alcohol as the raw material is more preferably a primary alcohol.

Specific examples of the preferred alcohol as the raw material include at least one alcohol selected from the group consisting of 1-dodecanol, 1-tridecanol, 1-tetradecanol, 1-pentadecanol, 1-hexadecanol, 1-heptadecanol, 1-octadecanol, 1-nonadecanol and 1-eicosanol, from the viewpoint of usefulness of the resulting olefins.

[Organic Solvent]

In the production process of the present invention, an organic solvent may be used, if required. The organic solvent usable in the present invention is not particularly limited as long as the organic solvent is kept in a liquid state at the reaction temperature and compatible with the substrate and the reaction product, and unless the organic solvent has no adverse influence on the reaction. The organic solvent may be in the form of a mixture of organic solvents. In addition, the organic solvent is preferably separable from the reaction product by utilizing a difference between boiling points thereof after completion of the reaction.

Examples of the preferred organic solvent usable in the present invention include hydrocarbon-based organic solvents such as a saturated aliphatic hydrocarbon, an unsaturated aliphatic hydrocarbon and an aromatic hydrocarbon.

The saturated aliphatic hydrocarbon may be either a straight-chain hydrocarbon or a branched hydrocarbon.

Specific examples of the saturated aliphatic hydrocarbon include compounds having not less than 10 and not more than 35 carbon atoms, such as tridecane, hexadecane, octadecane, eicosane, docosane, triacontane and squarane.

In addition, the saturated aliphatic hydrocarbon may also be in the form of a mixture such as liquid paraffin, naphthene-based hydrocarbons and isoparaffin-based hydrocarbons. Further, as the saturated aliphatic hydrocarbon, there may also be used solid paraffin that is kept in a solid state at a normal temperature but changed into a liquid state at the reaction temperature.

Furthermore, as the saturated aliphatic hydrocarbon, there may also be used oligomers of propylene, isobutene, etc.

The unsaturated aliphatic hydrocarbon may be either a straight-chain hydrocarbon or a branched hydrocarbon.

Specific examples of the unsaturated aliphatic hydrocarbon include compounds preferably having not less than 15 carbon atoms, and more preferably not less than 30 carbon atoms, and also preferably having not more than 35 carbon atoms, and more preferably not more than 30 carbon atoms, such as eicosene, heneicosene, docosene, tricosene and squalene. The unsaturated aliphatic hydrocarbon may be in the form of a mixture of unsaturated aliphatic hydrocarbons.

Specific examples of the aromatic hydrocarbon include alkyl benzenes and alkyl naphthalenes such as n-dodecyl benzene, n-tridecyl benzene, n-tetradecyl benzene, n-pentadecyl benzene, n-hexadecyl benzene and diisopropyl naphthalene.

[Dehydration Reaction (Olefination Reaction)]

The reaction used in the process of the present invention is a dehydration reaction of the alcohol. Therefore, in the reaction, if water by-produced stays or remains in the reaction system, the reaction rate tends to be lowered. For this reason, from the viewpoint of enhancing the reaction rate, an inert gas such as nitrogen and argon is preferably introduced into the reaction system while stirring under a reduced pressure of usually not less than 0.03 MPa and not more than 0.09 MPa or under normal pressures to conduct the reaction while removing the water produced in the reaction out of the reaction system.

The reaction temperature is preferably not higher than a boiling point of the alcohol as the raw material from the viewpoints of attaining a high reaction rate and suppressing occurrence of undesirable side reactions such as alkyl rearrangement and production of multimers of the olefins. More specifically, the reaction temperature is preferably not lower than 150° C., more preferably not lower than 200° C., still more preferably not lower than 220° C., even still more preferably not lower than 230° C., and further even still more preferably not lower than 270° C., from the viewpoints of suppressing occurrence of undesirable side reactions and attaining a high reaction rate, and is also preferably not higher than 350° C., more preferably not higher than 310° C., still more preferably not higher than 295° C., and even still more preferably not higher than 290° C., from the viewpoints of a high energy efficiency and a less burden on facilities.

In the present invention, the olefination reaction is preferably carried out in a liquid phase reaction. Meanwhile, the liquid phase reaction as used herein means a reaction that is carried out at a temperature not higher than a boiling point of the alcohol as the raw material, i.e., not higher than a temperature at which a liquid phase is still present. In the case where the olefination is carried out in the liquid phase reaction, it is not necessary to vaporize a whole amount of the raw material, and it is therefore possible to suppress increase in production costs. In addition, it is possible to suppress occurrence of branching of the olefins owing to alkyl rearrangement and production of multimers of the olefins and therefore produce the aimed product with a high yield.

From the viewpoint of a high yield of the olefins as the aimed product, the reaction time may be controlled such that the reaction rate of the alcohol is preferably not less than 95%, more preferably not less than 97%, and still more preferably not less than 98%. The reaction time may vary depending upon the reaction temperature, kind of the organic solvent used as well as kind and amount of the catalyst used, etc. In the suspended bed batch reaction, the reaction time is preferably not less than 0.1 h, more preferably not less than 0.5 h, and still more preferably not less than 1 h, and is also preferably not more than 20 h, more preferably not more than 10 h, and still more preferably not more than 7 h.

In the fixed bed reaction, from the viewpoint of a high yield, LHSV (liquid hourly space velocity) is preferably not less than 0.05/h, more preferably not less than 0.1/h, and still more preferably not less than 0.2/h. From the same viewpoint, LHSV is also preferably not more than 10/h, more preferably not more than 7/h, and still more preferably not more than 5/h.

According to the production process of the present invention, the reaction rate of the alcohol reaches usually not less than 80% and preferably not less than 90%, and the yield of the olefins reaches usually not less than 90%. In addition, the rate of production of branched olefins and dimers of olefins contained in the resulting olefins are respectively usually not more than 5%. Further, the olefins obtained by the production process of the present invention contain a high proportion of internally isomerized olefins, and it is therefore possible to readily obtain the aimed product containing the internally isomerized olefins in an amount of 30% or more on the basis of the whole olefins.

In the present invention, the olefins solely may be separated from the thus obtained reaction product by distillative purification. The high-purity olefins thus produced by distillative purification are useful as a raw material or an intermediate raw material for surfactants, organic solvents, softening agents, sizing agents, etc.

[Process for Producing Olefin Sulfonate]

The process for producing an olefin sulfonate according to the present invention includes the steps of sulfonating the olefins produced by the above process of the present invention to obtain a sulfonated product; and neutralizing the sulfonated product and then subjecting the resulting neutralized product to hydrolysis treatment.

The sulfonation reaction in the step of obtaining the sulfonated product may be carried out by reacting 1 mol of the olefins with preferably not less than 1 mol and not more than 1.2 mol of sulfur trioxide or sulfuric anhydride.

The reaction temperature used in the sulfonation reaction is preferably not lower than 0° C. and not higher than 40° C. from the viewpoint of a high yield.

When using sulfuric anhydride in the sulfonation reaction, the reaction temperature is preferably not lower than 0° C. and not higher than 20° C., and more preferably not lower than 0° C. and not higher than 10° C., from the viewpoint of a high yield.

In the step of subjecting the neutralized product to hydrolysis treatment, the neutralization may be carried out by reacting the neutralized product with an alkali aqueous solution such that the alkali aqueous solution is reacted in an amount of not less than 1 mol and not more than 1.5 mol per 1 mol of a stoichiometric amount of a sulfonic group in the neutralized product.

Examples of the alkali aqueous solution used in the neutralization include a sodium hydroxide aqueous solution, a potassium hydroxide aqueous solution, an ammonia aqueous solution, a 2-aminoethanol aqueous solution or the like.

The hydrolysis reaction may be carried out in the presence of water at a temperature of not lower than 90° C. and not higher than 200° C. for not less than 30 min and not more than 4 h.

The sulfonation reaction and the neutralization reaction may be carried out in a continuous manner. After completion of the neutralization reaction, the resulting product may be purified by extraction, washing, etc.

In addition to the aforementioned embodiments, the present invention provides the following aspects concerning the process for producing olefins.

<1> A process for producing olefins, including the step of subjecting an alcohol to dehydration reaction in the presence of a solid acid catalyst, in which the solid acid catalyst includes aluminum oxide and an oxide of an element having an electronegativity higher than that of aluminum which is supported on the aluminum oxide.

<2> The process for producing olefins according to the above aspect <1>, wherein an electronegativity of the oxide of the element is preferably not less than 1.6, more preferably not less than 1.7, and still more preferably not less than 1.8, and is also preferably not more than 2.6, and more preferably not more than 2.0.

<3> The process for producing olefins according to the above aspect <1> or <2>, wherein an amount of the oxide of the element supported on the aluminum oxide is preferably not less than 0.01% by mass, more preferably not less than 0.1% by mass, still more preferably not less than 0.5% by mass, and even still more preferably not less than 0.8% by mass, and is also preferably not more than 10% by mass, more preferably not more than 9% by mass, still more preferably not more than 8% by mass, even still more preferably not more than 7% by mass, and further even still more preferably not more than 2% by mass, on the basis of the amount of the aluminum oxide.

<4> The process for producing olefins according to any one of the above aspects <1> to <3>, wherein the element is at least one element selected from the group consisting of sulfur, tungsten, phosphorus and silicon.

<5> The process for producing olefins according to any one of the above aspects <1> to <4>, wherein a method of producing the catalyst by supporting the oxide of the element on the aluminum oxide includes the steps of mixing an aqueous suspension or a hydrous solid of the aluminum oxide, a compound as an oxide source of the element or the oxide of the element, and ion-exchanged water to prepare an impregnated product, and drying and calcining the resulting impregnated product.

<6> The process for producing olefins according to the above aspect <5>, wherein the compound as an oxide source of the element is preferably a water-soluble ammonium salt, a metal alkoxide, or an oxo acid or a salt thereof, more preferably at least one compound selected from the group consisting of ammonium sulfate, ammonium tungstate, tetraethyl orthosilicate and diammonium hydrogen phosphate, and still more preferably ammonium sulfate, ammonium tungstate, diammonium hydrogen phosphate or tetraethyl orthosilicate.

<7> The process for producing olefins according to the above aspect <5> or <6>, wherein the temperature at which the aluminum oxide is impregnated with the compound as an oxide source of the element or the oxide of the element is preferably not lower than 0° C., more preferably not lower than 20° C., still more preferably not lower than 50° C., and even still more preferably not lower than 60° C., and is also preferably not higher than 100° C., more preferably not higher than 95° C., still more preferably not higher than 90° C., and even still more preferably not higher than 80° C.

<8> The process for producing olefins according to any one of the above aspects <5> to <7>, wherein a temperature of calcination of the impregnated product is preferably not lower than 300° C., more preferably not lower than 400° C., still more preferably not lower than 450° C., and is also preferably not higher than 900° C., more preferably not higher than 850° C., still more preferably not higher than 800° C., even still more preferably not higher than 700° C., and further even still more preferably not higher than 600° C.

<9> The process for producing olefins according to any one of the above aspects <5> to <8>, wherein a time of calcination of the impregnated product is preferably not less than 1 h, and more preferably not less than 2 h, and is also preferably not more than 10 h, and more preferably not more than 5 h.

<10> The process for producing olefins according to any one of the above aspects <5> to <9>, wherein the calcination is carried out in an inert gas atmosphere, an oxidizing atmosphere or a reducing atmosphere.

<11> The process for producing olefins according to any one of the above aspects <5> to <10>, wherein the calcination is preferably carried out in a closed condition or in a gas-flowing condition, and more preferably carried out in a gas flow of air or oxygen.

<12> The process for producing olefins according to any one of the above aspects <1> to <11>, wherein the aluminum oxide is γ-alumina.

<13> The process for producing olefins according to any one of the above aspects <1> to <12>, wherein the catalyst is prepared by at least one method selected from the group consisting of an evaporation-to-dryness method, an adsorption method, an equilibrium adsorption method, a pore filling method, a spraying method and a precipitation method.

<14> The process for producing olefins according to any one of the above aspects <1> to <13>, wherein an average particle size of the catalyst is preferably not less than 1 μm, more preferably not less than 5 μm, still more preferably not less than 10 μm, even still more preferably not less than 20 μm, and further even still more preferably not less than 30 μm, and is also preferably not more than 300 μm, more preferably not more than 250 μm, still more preferably not more than 200 μm, even still more preferably not more than 150 μm, further even still more preferably not more than 100 μm, and further even still more preferably not more than 50 μm.

<15> The process for producing olefins according to any one of the above aspects <1> to <14>, wherein a BET specific surface area of the catalyst is preferably not less than 100 m$^2$/g, more preferably not less than 120 m$^2$/g, and still more preferably not less than 140 m$^2$/g, and is also preferably not more than 500 m$^2$/g, more preferably not more than 400 m$^2$/g, still more preferably not more than 300 m$^2$/g, and even still more preferably not more than 200 m$^2$/g.

<16> The process for producing olefins according to any one of the above aspects <1> to <15>, wherein an average pore size of the catalyst is preferably not less than 5 nm, more preferably not less than 7 nm, and still more preferably not less than 9 nm, and is also preferably not more than 50 nm, more preferably not more than 40 nm, still more preferably not more than 25 nm, even still more preferably not more than 20 nm, and further even still more preferably not more than 15 nm.

<17> The process for producing olefins according to any one of the above aspects <1> to <16>, wherein a pore volume of the catalyst is preferably not less than 0.20 cm$^3$/g, more preferably not less than 0.25 cm$^3$/g, and still more preferably not less than 0.30 cm$^3$/g, and is also preferably not more than 2.0 cm$^3$/g, more preferably not more than 1.5 cm$^3$/g, still more preferably not more than 1.2 cm$^3$/g, even still more preferably not more than 1.0 cm$^3$/g, and further even still more preferably not more than 0.7 cm$^3$/g.

<18> The process for producing olefins according to any one of the above aspects <1> to <17>, wherein the alcohol is a primary alcohol.

<19> The process for producing olefins according to any one of the above aspects <1> to <18>, wherein the number of carbon atoms contained in the alcohol is preferably not less than 8, more preferably not less than 12, and still more preferably not less than 14, and is also preferably not more than 22, more preferably not more than 20, and still more preferably not more than 18.

<20> The process for producing olefins according to any one of the above aspects <1> to <19>, wherein the number of carbon atoms contained in the alcohol is not less than 8 and not more than 22, preferably not less than 12 and not more than 20, and more preferably not less than 14 and not more than 18.

<21> The process for producing olefins according to any one of the above aspects <1> to <20>, wherein the dehydration reaction is carried out while removing water produced therein out of the reaction system.

<22> The process for producing olefins according to any one of the above aspects <1> to <21>, wherein the dehydration reaction is carried out while introducing an inert gas into the reaction system.

<23> The process for producing olefins according to any one of the above aspects <1> to <22>, wherein the dehydration reaction is carried out under a reduced pressure of not less than 0.03 MPa and not more than 0.09 MPa or under normal pressures.

<24> The process for producing olefins according to any one of the above aspects <1> to <23>, wherein the dehydration reaction is preferably carried out at a temperature not higher than a boiling point of the alcohol as the raw material, more specifically, carried out at a temperature of preferably not lower than 150° C., more preferably not lower than 200° C., still more preferably not lower than 220° C., even still more preferably not lower than 230° C., and further even still more preferably not lower than 270° C., and also preferably not higher than 350° C., more preferably not higher than 310° C., still more preferably not higher than 295° C., and even still more preferably not higher than 290° C.

<25> The process for producing olefins according to any one of the above aspects <1> to <24>, wherein the dehydration reaction is carried out in a liquid phase.

EXAMPLES

Catalyst Preparation Example 1

A 500 mL eggplant shaped flask was charged with 10.0 g of aluminum oxide "GP-20" (available from Mizusawa Industrial Chemicals, Ltd.; BET specific surface area: 189 m$^2$/g; average particle size: 33 µm; average pore size: 12.1 nm; pore volume: 0.44 cm$^3$/g), 0.69 g of ammonium sulfate (available from Wako Pure Chemical Industries, Ltd.; 5% by mass in terms of $SO_4$ on the basis of aluminum oxide) and 100 g of ion-exchanged water, and water is evaporated to dryness using a rotary evaporator (70° C.; 30 mmHg). The resulting powder was dried at 120° C. for 12 h, and calcined in air at 500° C. for 3 h, thereby preparing a solid acid catalyst. The resulting solid acid catalyst had a BET specific surface area of 162 m$^2$/g, an average particle size of 36 µm, an average pore size of 11.8 nm and a pore volume of 0.41 cm$^3$/g.

Catalyst Preparation Example 2

The same procedure as in Catalyst Preparation Example 1 was repeated except for using 0.56 g of ammonium tungstate (available from Wako Pure Chemical Industries, Ltd.; 5% by mass in terms of $WO_3$ on the basis of aluminum oxide) in place of ammonium sulfate, thereby preparing a solid acid catalyst. The resulting solid acid catalyst had a BET specific surface area of 159 m$^2$/g, an average particle size of 34 µm, an average pore size of 11.7 nm and a pore volume of 0.40 cm$^3$/g.

Catalyst Preparation Example 3

The same procedure as in Catalyst Preparation Example 1 was repeated except for using 0.65 g of diammonium hydrogen phosphate (available from Wako Pure Chemical Industries, Ltd.; 5% by mass in terms of $PO_4$ on the basis of aluminum oxide) in place of ammonium sulfate, thereby preparing a solid acid catalyst. The resulting solid acid catalyst had a BET specific surface area of 154 m$^2$/g, an average particle size of 33 µm, an average pore size of 11.9 nm and a pore volume of 0.41 cm$^3$/g.

Catalyst Preparation Example 4

The same procedure as in Catalyst Preparation Example 1 was repeated except for using 1.73 g of tetraethyl orthosilicate (available from Wako Pure Chemical Industries, Ltd.; 5% by mass in terms of $SiO_2$ on the basis of aluminum oxide) and 0.2 g of a 0.1 N nitric acid aqueous solution in place of ammonium sulfate, thereby preparing a solid acid catalyst. The resulting solid acid catalyst had a BET specific surface area of 158 m$^2$/g, an average particle size of 38 µm, an average pore size of 11.8 nm and a pore volume of 0.42 cm$^3$/g.

Catalyst Preparation Example 5

The same procedure as in Catalyst Preparation Example 1 was repeated except for using the ammonium sulfate (available from Wako Pure Chemical Industries, Ltd.; 1% by mass in terms of $SO_4$ on the basis of aluminum oxide) in an amount of 0.14 g, thereby preparing a solid acid catalyst. The resulting solid acid catalyst had a BET specific surface area of 164 m$^2$/g, an average particle size of 35 µm, an average pore size of 11.9 nm and a pore volume of 0.42 cm$^3$/g.

Catalyst Preparation Example 6

The same procedure as in Catalyst Preparation Example 1 was repeated except for using 0.12 g of ammonium tungstate (available from Wako Pure Chemical Industries, Ltd.; 1% by mass in terms of $WO_3$ on the basis of aluminum oxide) in place of ammonium sulfate, thereby preparing a solid acid catalyst. The resulting solid acid catalyst had a BET specific surface area of 152 m$^2$/g, an average particle size of 36 µm, an average pore size of 12.0 nm and a pore volume of 0.41 cm$^3$/g.

Catalyst Preparation Example 7

The same procedure as in Catalyst Preparation Example 1 was repeated except for using 0.35 g of tetraethyl orthosilicate (available from Wako Pure Chemical Industries, Ltd.; 1% by mass in terms of $SiO_2$ on the basis of aluminum oxide) and 0.1 g of a 0.1 N nitric acid aqueous solution in place of ammonium sulfate, thereby preparing a solid acid catalyst. The resulting solid acid catalyst had a BET specific surface area of 110 m²/g, an average particle size of 35 μm, an average pore size of 11.9 nm and a pore volume of 0.41 cm³/g.

Comparative Catalyst Preparation Example 1

The same procedure as in Catalyst Preparation Example 1 was repeated except for using 1.25 g of cerium nitrate (available from Wako Pure Chemical Industries, Ltd.; 5% by mass in terms of $CeO_2$ on the basis of aluminum oxide) in place of ammonium sulfate, thereby preparing a solid acid catalyst. The resulting solid acid catalyst had a BET specific surface area of 154 m²/g, an average particle size of 35 μm, an average pore size of 11.9 nm and a pore volume of 0.41 cm³/g.

Comparative Catalyst Preparation Example 2

The same procedure as in Catalyst Preparation Example 1 was repeated except for using 1.33 g of lanthanum nitrate (available from Wako Pure Chemical Industries, Ltd.; 2.5% by mass in terms of $La_2O_3$ on the basis of aluminum oxide) in place of ammonium sulfate, thereby preparing a solid acid catalyst. The resulting solid acid catalyst had a BET specific surface area of 159 m²/g, an average particle size of 34 μm, an average pore size of 11.9 nm and a pore volume of 0.42 cm³/g.

Example 1

[Olefination Reaction]

A 100 mL four-necked flask equipped with a stirrer was charged with 50.0 g (0.19 mol) of 1-octadecanol "KALCOL 8098" (available from Kao Corp.) and 1.5 g (3% by mass on the basis of alcohol) of the solid acid catalyst prepared in Catalyst Preparation Example 1, and the contents of the flask were reacted at 280° C. for 1 h under stirring while flowing nitrogen through the reaction system (nitrogen flow rate: 50 mL/min).

After completion of the reaction, the resulting reaction solution was diluted with hexane, and the resulting dilute solution was analyzed using a gas chromatographic analyzer "HP6890" (available from HEWLETT PACKARD Co.) equipped with a column "Ultra ALLOY-1" (available from Frontier Laboratories Ltd.; capillary column; 30.0 m×250 μm) and a flame ionization detector (FID) under the conditions of injection temperature: 300° C.; detector temperature: 350° C.; flow rate of He: 4.6 mL/min, to conduct quantitative determination of the resulting reaction product. The results are shown in Table 1.

Meanwhile, the yield of the olefins was calculated according to the following formula.

Yield (%) of Olefins=[{amount of olefins (mol)/amount of alcohol as raw material charged (mol)}]×100

Examples 2 to 9 and Comparative Examples 1 to 4

[Olefination Reaction]

The reaction was carried out in the same manner as in Example 1 except that the catalyst and the reaction conditions used therein were changed as shown in Table 1, and the reaction solution obtained after completion of the reaction was subjected to the measurement. The reaction conditions and the results are collectively shown in Table 1. Meanwhile, in Comparative Example 1, only the aluminum oxide used in Catalyst Preparation Example 1 was used as the catalyst.

TABLE 1

|  | Examples | | | | | | | | | Comparative Examples | | | |
| --- | --- | --- | --- | --- | --- | --- | --- | --- | --- | --- | --- | --- | --- |
|  | 1 | 2 | 3 | 4 | 5 | 6 | 7 | 8 | 9 | 1 | 2 | 3 | 4 |
| Catalyst | *a | *b | *c | *d | *e | *f | *g | *f | *g | *h | *i | *j | *k |
| Element supported | S | W | P | Si | S | W | Si | W | Si | — | Ce | La | — |
| Electronegativity | 2.5 | 1.7 | 2.1 | 1.8 | 2.5 | 1.7 | 1.8 | 1.7 | 1.8 | — | 1.1 | 1.1 | — |
| Amount supported*[1] (mass %) | 5 | 5 | 5 | 5 | 1 | 1 | 1 | 1 | 1 | — | 5 | 5 | — |
| Alcohol as raw material | *l | *l | *l | *l | *l | *l | *l | *m | *m | *l | *l | *l | *l |
| Amount of catalyst*[2] (mass %) | 3 | 3 | 3 | 3 | 3 | 3 | 3 | 10 | 10 | 3 | 3 | 3 | 3 |
| Reaction temperature (° C.) | 280 | 280 | 280 | 280 | 280 | 280 | 280 | 240 | 240 | 280 | 280 | 280 | 280 |
| Reaction time (h) | 1 | 5 | 5 | 3 | 5 | 5 | 4 | 8 | 6 | 5 | 5 | 5 | 2 |
| Yield of olefins (%) | 89 | 80 | 76 | 94 | 94 | 98 | 96 | 97 | 94 | 57 | 10 | 6 | 84 |
| Rate of production of dimer (%) | 6.8 | 4.3 | 5.0 | 6.1 | 4.3 | 1.5 | 3.5 | 2.1 | 3.9 | 3.4 | 1.0 | 0.0 | 16.0 |
| Selectivity to monomeric olefins (%) | 93 | 95 | 94 | 94 | 96 | 98 | 96 | 98 | 96 | 94 | 91 | 100 | 84 |

Note
*a: Catalyst Preparation Example 1;
*b: Catalyst Preparation Example 2;
*c: Catalyst Preparation Example 3;
*d: Catalyst Preparation Example 4;
*e: Catalyst Preparation Example 5;
*f: Catalyst Preparation Example 6;
*g: Catalyst Preparation Example 7;
*h: Aluminum oxide;
*i: Comparative Catalyst Preparation Example 1;
*j: Comparative Catalyst Preparation Example 2;
*k: Silica-alumina*[3];
*l: Octadecanol;
*m: Tetradecanol
*[1]Value in terms of an oxide on the basis of aluminum oxide
*[2]Amount on the basis of alcohol as a raw material
*[3]Available from JGC Catalysts and Chemicals Ltd.; Si/Al = 81/19 (molar ratio)

From the results of Table 1, it was confirmed that when using the catalyst on which the element having an electronegativity higher than that of aluminum was supported, the olefins were produced with a very high yield.

As described above, according to the production process of the present invention, it is possible to produce long-chain olefins with a high yield for a short period of time by subjecting a long-chain aliphatic primary alcohol to dehydration reaction.

Example 10

[Sulfonation Reaction]
Step of Obtaining Sulfonated Product

A 3000 mL four-necked flask was equipped with a mechanical stirrer and a thermometer and further with two dropping funnels. An inside of the four-necked flask was held under reduced pressure, and then purged with nitrogen to return an inside pressure of the flask to atmospheric pressure. Then, 211 g of 1,4-dioxane (available from Wako Pure Chemical Industries, Ltd.) and 975 g of chloroform (available from Wako Pure Chemical Industries, Ltd.) were charged into the flask. The obtained reaction solution in the four-necked flask was cooled to a temperature of 5° C. or lower in an ice bath. After cooling, 56.8 g of sulfuric anhydride (sulfur trioxide) "NISSO SULFAN" (available from Nisso Metallochemical Co., Ltd.) was added dropwise to the flask through a dropping funnel over 1 h. After completion of the dropwise addition, the contents of the flask were stirred for 0.5 h. Thereafter, 152 g of the olefins produced in Example 5 were added dropwise to the flask through a dropping funnel over 1 h.
Steps of Neutralization and Hydrolysis Treatment A 3000 mL SUS beaker was charged with 119 g of a 48% by mass sodium hydroxide aqueous solution and 302 g of ion-exchanged water, and the contents of the beaker were cooled in an ice bath. After sufficiently cooling, while continuously cooling the contents of the beaker in an ice bath, the reaction solution obtained in the above reaction step was gradually added to the beaker while stirring the contents of the beaker using a homomixer. After charging a whole amount of the reaction solution obtained in the above reaction step into the beaker, the contents of the beaker were stirred at 5000 rpm for 3 h.

The reaction solution obtained in the neutralization step was filled in an eggplant-shaped flask, and while heating the contents of the flask in a hot water bath at 55° C., chloroform, 1,4-dioxane and water were distilled off therefrom using a rotary evaporator. The resulting concentrated product was mixed with 670 g of ion-exchanged water to prepare an aqueous solution containing sodium olefin sulfonate at a concentration of 40% by mass. Then, 400 g of the thus prepared aqueous solution was charged into a 1 L autoclave and reacted at 160° C. for 3 h, thereby obtaining 385 g of a sodium olefin sulfonate aqueous solution.

The content of effective ingredients in the thus obtained sodium olefin sulfonate aqueous solution was 16% by mass. Meanwhile, the content of the effective ingredients in the aqueous solution was determined by a potentiometric titration method using a benzethonium chloride solution (JIS K3362 "Testing Method for Synthetic Detergents").

The invention claimed is:

1. A process for producing olefins, comprising the step of subjecting an alcohol having not less than 8 and not more than 22 carbon atoms to dehydration reaction in the presence of a solid acid catalyst, in which the solid acid catalyst comprises aluminum oxide and an oxide of an element having an electronegativity higher than that of aluminum which is supported on the aluminum oxide,
wherein the dehydration reaction is a liquid phase reaction,
wherein the element is at least one element selected from the group consisting of sulfur, tungsten, and phosphorus,
wherein an amount of the oxide of the element supported on the aluminum oxide is not less than 0.8% by mass and not more than 5% by mass on the basis of the amount of the aluminum oxide, and
wherein the dehydration reaction is carried out at a temperature of not lower than 200° C. and not higher than 310° C.

2. The process for producing olefins according to claim 1, wherein the aluminum oxide is γ-alumina.

3. The process for producing olefins according to claim 1, wherein the alcohol is a primary alcohol.

4. The process for producing olefins according to claim 1, wherein the alcohol is at least one alcohol selected from the group consisting of 1-dodecanol, 1-tridecanol, 1-tetradecanol, 1-pentadecanol, 1-hexadecanol, 1-heptadecanol, 1-octadecanol, 1-nonadecanol and 1-eicosanol.

5. The process for producing olefins according to claim 1, wherein a method of producing the catalyst by supporting the oxide of the element on the aluminum oxide comprises the steps of mixing an aqueous suspension or a hydrous solid of the aluminum oxide, a compound as an oxide source of the element or the oxide of the element, and ion-exchanged water to prepare an impregnated product, and drying and calcining the resulting impregnated product.

6. The process for producing olefins according to claim 5, wherein the compound as an oxide source of the element is a water-soluble ammonium salt, a metal alkoxide, or an oxo acid or a salt thereof.

7. The process for producing olefins according to claim 5, wherein the compound as an oxide source of the element is ammonium sulfate, ammonium tungstate or diammonium hydrogen phosphate.

8. The process for producing olefins according to claim 1, wherein the dehydration reaction is carried out while removing water produced therein out of the reaction system.

9. The process for producing olefins according to claim 8, wherein the dehydration reaction is carried out while introducing an inert gas into the reaction system.

10. The process for producing olefins according to claim 1, wherein the BET specific surface area of the catalyst is not less than 100 m$^2$/g and not more than 500 m$^2$/g.

11. The process for producing olefins according to claim 1, wherein the average pore size of the catalyst is not less than 5 nm and not more than 50 nm.

12. The process for producing olefins according to claim 1, wherein the pore volume of the catalyst is not less than 0.20 cm$^3$/g and not more than 2.0 cm$^3$/g.

13. A process for producing an olefin sulfonate, comprising the steps of:
sulfonating the olefins produced by the process as claimed in claim 1 to obtain a sulfonated product; and
neutralizing the sulfonated product and then subjecting the resulting neutralized product to hydrolysis treatment.

14. A process for producing olefins, comprising the step of subjecting an alcohol having not less than 8 and not more than 22 carbon atoms to dehydration reaction in the presence of a solid acid catalyst, in which the solid acid catalyst comprises aluminum oxide and an oxide of an element having an electronegativity higher than that of aluminum which is supported on the aluminum oxide, wherein an amount of the oxide of the element supported on the aluminum oxide is not less than 0.8% by mass and not more than 5% by mass on the basis of the aluminum oxide, wherein the dehydration reaction is a liquid phase reaction, wherein a method of producing the catalyst by supporting the oxide of the element on the aluminum oxide comprises the steps of mixing an aqueous suspension or a hydrous solid of the aluminum oxide, a compound as an oxide source of the element or the oxide of the element, and ion-exchanged water to prepare an impregnated product, and drying and calcining the resulting impregnated product, wherein the dehydration reaction is carried out at a temperature of not lower than 200° C. and not higher than 310° C., and wherein the process does not utilize an organic solvent therein.

15. The process for producing olefins according to claim 14, wherein the alcohol is at least one alcohol selected from the group consisting of 1-dodecanol, 1-tridecanol, 1-tetradecanol, 1-pentadecanol, 1-hexadecanol, 1-heptadecanol, 1-octadecanol, 1-nonadecanol and 1-eicosanol, and wherein the compound as an oxide source of the element is ammonium sulfate, ammonium tungstate, diammonium hydrogen phosphate or tetraethyl orthosilicate.

* * * * *